United States Patent [19]

Jung et al.

[11] Patent Number: 4,490,382

[45] Date of Patent: Dec. 25, 1984

[54] PENICILLIN DERIVATIVES

[75] Inventors: Frédéric H. Jung, Rilly la Montagne, France; Gareth M. Davies, Cheshire, England

[73] Assignees: Imperial Chemical Industries PLC, London, England; ICI Pharma, Enghien les Bains, France

[21] Appl. No.: 333,567

[22] Filed: Dec. 22, 1981

[30] Foreign Application Priority Data

Dec. 23, 1980 [FR] France ............................ 80 27336

[51] Int. Cl.³ ............... C07D 277/20; A61K 31/425
[52] U.S. Cl. ...................... 424/270; 260/245.2 R; 260/245.2 T; 424/251; 424/273 R
[58] Field of Search ........... 260/245.2 R, 245.2 T; 424/270, 251, 273 R

[56] References Cited

U.S. PATENT DOCUMENTS 4,283,402 7/1981 Hannah ................ 260/245.2 R
4,358,447 11/1982 Hannah .......................... 544/22

FOREIGN PATENT DOCUMENTS 31708 8/1981 European Pat. Off. .
78/7340 1/1978 South Africa .
434264 4/1964 Switzerland .

Primary Examiner—Nicholas S. Rizzo
Attorney, Agent, or Firm—Cushman, Darby & Cushman

[57] ABSTRACT

A penicillin derivative of the formula I:

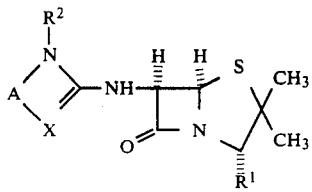

in which $R^1$ is any one of the C-3 substituents from antibacterially-active penicillins known in the art;

X is a nitrogen atom or a radical of the formula $N^{\oplus}-R^3$;

$R^2$ and $R^3$, which may be the same or different, are hydrogen atoms or 1-6C alkyl, 1-6C alkanoyl, hydroxy, 1-6C alkoxy, amino, 1-6C alkanoylamino, 1-6C alkylamino, 1-6C aminoalkyl, 1-6C hydroxyalkyl, 2-6C carboxyalkyl, 2-6C alkenyl, 3-6C alkoxyalkyl, 3-8C alkoxycarbonylalkyl, furylmethyl, phenyl or 7-11C phenylalkyl radicals, in the latter two of which the phenyl ring is optionally substituted by a halogen atom or by a methyl, methoxy, nitro, hydroxy, amino, carboxy or methoxy-carbonyl radical;

A< is a radical of the formula II or III:

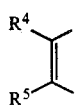

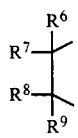

in which $R^4$, $R^5$, $R^6$, $R^7$, $R^8$ and $R^9$ are as described in the specification; and the pharmaceutically-acceptable acid- or base-addition salts thereof. Pharmaceutical compositions and manufacturing processes are also described.

6 Claims, No Drawings

PENICILLIN DERIVATIVES

This invention relates to penicillin derivatives which have antibacterial properties.

The vast majority of therapeutically-useful antibiotics based on the penicillin and cephalosporin ring systems have an acylamino radical at the 6β and 7β positions respectively. A number of other substituents at these positions have been investigated, but in the main the resulting compounds have at best possessed only weak antibacterial activity. One exception to this generalisation is the amidino substituent. Penicillin derivatives carrying a substituted amidino radical in the 6β-position (see for example U.K. Pat. Nos. 1,315,566 and 1,406,732) have been found to have useful antibacterial activity and two such compounds, mecillinam and pivmecillinam, are commercially available.

European patent publication No. 18595 describes a series of cephalosporin derivatives carrying a 2- or 4-pyridinioamino radical in the 7-position. Swiss patent No. 434,264 describes pencillin derivatives carrying a 1,3,5-triazin-2-ylamino radical in the 6-position.

European patent publication No. 31708 describes a series of cephalosporin derivatives carrying a 7-(imidazolin-2-yl)amino or 7-(imidazol-2-yl)amino radical. The present application represents an extension of this work to the penicillin nucleus.

According to the invention there is provided a penicillin derivative of the formula I:

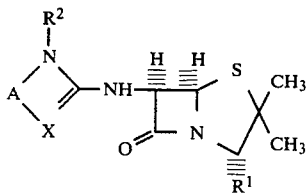

in which
R$^1$ is any one of the C-3 substituents from antibacterially-active penicillins known in the art;
X is a nitrogen atom or a radical of the formula N$^\oplus$-R$^3$;
R$^2$ and R$^3$, which may be the same or different, are hydrogen atoms or 1-6C alkyl, 1-6C alkanoyl, hydroxy, 1-6C alkoxy, amino, 1-6C alkanoylamino, 1-6C alkylamino, 1-6C aminoalkyl, 1-6C hydroxyalkyl, 2-6C carboxyalkyl, 2-6C alkenyl, 3-6C alkoxyalkyl, 3-8C alkoxycarbonylalkyl, furylmethyl, phenyl or 7-11C phenylalkyl radicals, in the latter two of which the phenyl ring is optionally substituted by a halogen atom or by a methyl, methoxy, nitro, hydroxy, amino, carboxy or methoxycarbonyl radical;
A< is a radical of the formula II or III:

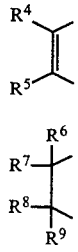

in which R$^4$ and R$^5$, which may be the same or different, are 1-6C haloalkyl, 1-6C azidoalkyl, 2-6C cyanoalkyl, 2-6C carboxyalkyl, 3-8C alkoxycarbonylalkyl, 2-6C carbamoylalkyl, 3-8C alkylcarbamoylalkyl, 4-10C dialkylcarbamoylalkyl, 2-6C (amino)(carboxy)alkyl, 2-6C alkenyl, 2-6C nitroalkenyl, 8-15C arylalkenyl, 14-25C diarylalkenyl, 20-35C triarylalkenyl, 1-6C alkylthio, 2-6C aminoalkylthio, 3-8C alkylaminoalkylthio, 4-12C dialkylaminoalkylthio, 2-6C aminoalkoxy, 3-8C alkylaminoalkoxy, 4-12C dialkylaminoalkoxy, 6-10C arylthio, 6-10C aryloxy, 7-11C arylalkyl, amino, 1-6C alkylamino, 2-8C dialkylamino, 6-10C arylamino, 7-11C arylalkylamino, 12-20C diarylamino, 1-6C alkanoyl, 7-11C aroyl, 2-6C alkoxycarbonylamino, 7-11C aryloxycarbonylamino, 2-6C alkoxythiocarbonylamino, 7-11C aryloxythiocarbonylamino, 1-6C alkanoylamino, 7-11C aroylamino, 2-6C alkylureido, 7-11C arylureido, 3-8C hydroxyalkenyl, carbamoyl, 2-6C alkylcarbamoyl, 3-8C dialkylcarbamoyl, 5-10C (dialkylaminoalkyl)carbamoyl, 7-11C arylcarbamoyl, thiocarbamoyl, 2-6C (alkyl)thiocarbamoyl, 3-8C (dialkyl)thiocarbamoyl, 7-11C (aryl)thiocarbamoyl, 5-10C (dialkylaminoalkyl)thiocarbamoyl, 2-6C alkoxyalkyl, 2-6C alkanoyloxyalkyl, 2-6C carbamoyloxyalkyl, 3-8C alkylcarbamoyloxyalkyl, 4-12C dialkylcarbamoyloxyalkyl, 7-11C (aryl)(hydroxy)alkyl, 7-11C (aryl)(amino)alkyl, 2-6C alkanoylaminoalkyl, 3-8C haloalkanoylaminoalkyl, 8-15C aroylaminoalkyl, 2-6C ureidoalkyl, 3-8C (alkylureido)alkyl, 4-12C (dialkylureido)alkyl, 8-15C (arylureido)alkyl, 2-6C guanidinoalkyl, 2-6C formimidoylaminoalkyl, 3-8C alkylimidoylaminoalkyl, 1-6C alkoxy, 2-6C formylalkyl, 2-10C alkanesulphonylaminoalkyl or 7-15C arenesulphonylaminoalkyl radicals, or R$^4$ and R$^5$ are 2-6C alkyl radicals which are substituted on different carbon atoms by two radicals selected from hydroxy, nitro, amino, 1-6C alkylamino, 2-8C dialkylamino, 6-10C arylamino, 7-11C arylalkylamino, 7-15C (aryl)(alkyl)amino, 8-20C (arylalkyl)(alkyl)amino, pyrrolidino, piperidino, piperazino, N-methylpiperazino, morpholino, 1-6C alkoxy, 1-6C alkylthio, 6-10C aryloxy, 6-10C arylthio, 7-11C arylalkoxy and 7-11C arylalkylthio radicals, or R$^4$ and R$^5$ are 2-6C alkyl radicals which are substituted on one carbon atom by a nitro, amino, 1-6C alkylamino, 2-10C dialkylamino or 1-6C alkanoylamino radical and on a different carbon atom by a methyl radical which is itself substituted by two radicals selected from cyano, 2-6C alkoxycarbonyl and 1-6C alkanoyl radicals,
or R$^4$ and R$^5$ are radicals of the formula IV, V, VI, VII, VIII, IX or X:

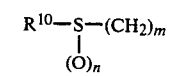

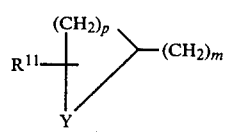

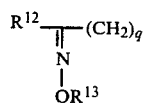

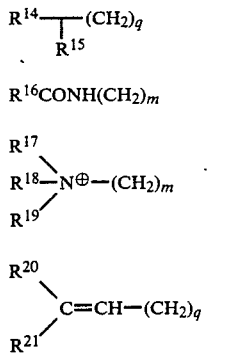

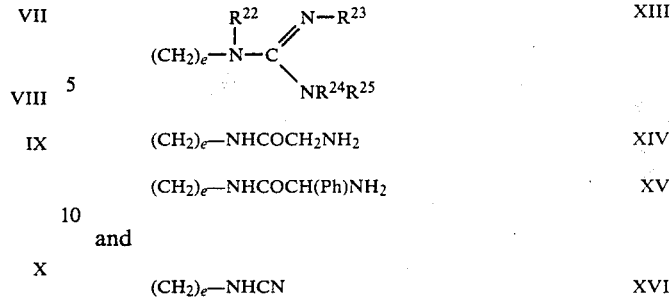

in which Y is an oxygen or sulphur atom or a $CH_2$ radical, m is 1 to 6, q is 0 to 6, n is 0, 1 or 2, p is 1 to 4, $R^{10}$ is a 1-6C alkyl, 6-10C aryl or 7-11C aralkyl radical, $R^{11}$ is a hydrogen atom or a 1-6C alkyl or 6-10C aryl, $R^{12}$ is a hydrogen atom or 1-6C alkyl, 6-10C aryl, 7-11C arylalkyl or heterocyclyl radical, $R^{13}$ is a hydrogen atom or a 1-6C alkyl radical which is optionally substituted by a carboxy, 2-6C alkoxycarbonyl, carbamoyl or cyano radical, $R^{14}$ is a heterocyclyl radical, $R^{15}$ is a hydroxy or amino radical, $R^{16}$ is a pyridyl radical, $R^{17}$, $R^{18}$ and $R^{19}$, which may be the same or different, are hydrogen atoms or 1-6C alkyl or 6-10C aryl radicals and $R^{20}$ and $R^{21}$, which may be the same or different, are cyano, nitro, 2-6C alkoxycarbonyl, 7-11C aryloxycarbonyl, 1-6C alkanoyl or 7-11C aroyl radicals, or $R^4$ and $R^5$ are heterocyclic radicals which are linked (to the imidazole ring) by a direct bond or by a methylene or thiomethylene ($SCH_2$) bridge, or $R^4$ or $R^5$ is a hydrogen or halogen atom or a 1-6C alkyl, cyano, hydroxy, carboxy, 2-6C alkoxycarbonyl, 1-6C aminoalkyl, 2-10C alkylaminoalkyl, 3-15C dialkylaminoalkyl or 1-6C hydroxyalkyl radical, or a phenyl radical optionally substituted by 1 or 2 radicals selected from halogen atoms and nitro, amino, hydroxy, carboxy, cyano, 1-6C alkyl and 2-6C alkoxycarbonyl radicals;

or $R^4$ and $R^5$ are joined to form, together with the carbon atoms to which they are attached, a mono-, bi- or tri-cyclic carbocyclic ring system which may be non aromatic, partially aromatic or fully aromatic, the aromatic part of such a ring system being optionally substituted by 1, 2 or 3 radicals selected from halogen atoms and hydroxy, amino, cyano, carboxy, carbamoyl, nitro, ureido, 1-6C alkyl, 1-6C alkoxy, 1-6C haloalkyl, 1-6C alkylamino, 1-6C hydroxyalkyl, 1-6C aminoalkyl, 1-6C alkanoylamino, 1-6C azidoalkyl, 2-6C dialkylamino, 2-10C alkylaminoalkyl, 3-15C dialkylaminoalkyl, 2-6C cyanoalkyl, 2-6C carboxyalkyl, 2-6C carbamoylalkyl and 2-6C ureidoalkyl radicals and radicals of the formula XI, XII, XIII, XIV, XV and XVI:

$OCONH_2$      XI

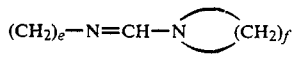
     XII $(CH_2)_e-NHCOCH_2NH_2$      XIV $(CH_2)_e-NHCOCH(Ph)NH_2$      XV and $(CH_2)_e-NHCN$      XVI in which e is 0 to 6, f is 4 to 8 and $R^{22}$, $R^{23}$, $R^{24}$ and $R^{25}$, which may be the same or different, are hydrogen atoms or 1-6C alkyl radicals;

and $R^6$, $R^7$, $R^8$ and $R^9$, which may be the same or different, are selected from hydrogen atoms and carboxy, cyano, pyridyl, 1-6C alkanoyl, 1-6C hydroxyalkyl, 1-10C alkyl, 7-12C phenoxyalkyl, (in which the phenyl part is optionally substituted by a diphenylmethyl) and phenyl radicals, the phenyl radicals being optionally substituted by 1, 2 or 3 radicals selected from halogen atoms and cyano, amino, carboxy, carbamoyl, hydroxy, phenyl, phenoxy, diphenylmethyl, 1-6C alkylamino, 1-6C alkanoylamino, 1-6C alkanesulphonylamino, 1-6C aminoalkyl, 1-6C hydroxyalkyl, 2-10C dialkylamino, 2-6C alkoxycarbonyl, 2-6C alkylcarbamoyl and 3-10C dialkylcarbamoyl radicals, or $R^7$ and $R^8$, when in the cis relationship, are joined to form, together with the carbon atoms to which they are attached, a 3 to 6 membered carbocyclic ring, the ring being optionally substituted by 1 or 2 radicals selected from phenyl and 1-6C haloalkyl radicals and the 4 to 6 membered rings optionally containing a double bond in a position other than at the ring fusion:

wherein when $R^4$ or $R^5$ contains an aryl radical, that aryl radical may optionally be substituted by 1 or 2 radicals selected from halogen atoms and nitro, amino, hydroxy, carboxy, cyano, 1-6C alkyl, 2-6C alkoxycarbonyl, sulpho, 1-6C alkoxy, 1-6C haloalkyl, 1-6C alkylsulphamoyl and 2-8C dialkylsulphamoyl radicals;

and wherein when $R^4$ or $R^5$ is, or contains, a heterocyclic radical, that radical is a 5- or 6-membered aromatic or non-aromatic heterocycle which contains 1, 2, 3, or 4 hetero atoms selected from N, O and S, such ring where possible optionally being in the form of the N-oxide, such a ring being optionally fused with a benzene ring and such fused benzene ring and/or (where possible) the heterocyclic ring being optionally substituted by one or two substituents selected from halogen atoms and 1-6C alkyl, hydroxy, 1-6C alkoxy, phenoxy, mercapto, 1-6C alkylthio, phenylthio, carboxy, 2-6C alkoxycarbonyl, phenoxycarbonyl, carbamoyl, 2-6C alkylcarbamoyl, 3-10C dialkylcarbamoyl, phenylcarbamoyl, diphenylcarbamoyl, nitro, amino, 1-6C alkylamino, 2-8C dialkylamino, phenylamino, 7-12C (phenyl)(alkyl)amino, diphenylamino, carboxyamino, 2-6C (carboxy)(alkyl)amino, (carboxy)(phenyl)amino, 1-6C alkanoylamino, 2-10C (alkanoyl)(alkyl)amino, benzoylamino, 8-14C (benzoyl)(alkyl)amino, cyano, phenyl, sulphamoyl, 1-6C alkylsulphamoyl, 2-10C dialkylsulphamoyl, phenylsulphamoyl, 1-6C haloalkyl, 1-6C aminoalkyl, 2-8C alkylaminoalkyl, 3-12C dialkylaminoalkyl, 2-6C carboxyalkyl and 1-6C sulphoalkyl radicals;

and where the compound of the formula I contains a free basic or acidic group, the pharmaceutically acceptable acid- or base-addition salts thereof.

It is to be understood that in the above formula I and throughout this specification, the illustrated stereochemistry of the penam nucleus of the formula XVII:

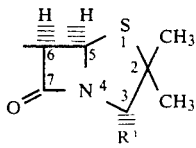
XVII is the absolute configuration. It is also to be understood that, although the double bonds in formulae I and II have been inserted in particular positions, other tautomeric forms are, in certain instances, possible, and these other forms are included within the scope of the invention. It is also to be understood that when the compound of the formula I contains both an acidic or basic centre, the compound may exist in the form of a zwitterion.

It will also be observed that, when $A<$ is a radical of the formula III, the compound of the formula I may contain 1 or 2 carbon atoms, each of which carries non-identical atoms or radicals $R^6$ and $R^7$ and $R^8$ and $R^9$. When one such carbon atom is present, the compound of the formula I will exist in 2 diastereoisomeric forms. When two such carbon atoms are present, the compound of the formula I will exist in 4 diastereoisomeric forms. It is to be understood that the useful properties, as hereinafter defined, of these diastereoisomers may differ and it is therefore to be understood that when $A<$ is a radical of the formula III, this invention encompasses the diastereoisomeric mixture represented by the formula I and any individual diastereoisomer which possesses the useful properties, it being a matter of common general knowledge how to obtain such individual diastereoisomers and determine the biological properties of each. Similar remarks apply when the compound of the formula I contains an asymmetric centre in another part of the molecule.

A particular value for $R^1$ is a carboxy radical on a radical of the formula XVIII, XIX, XX, XXI, XXII, XXIII, XXIV, XXV, XXVI, XXVII, XXVIII or XXIX:

| | |
|---|---|
| COOCHR²⁶OCOR²⁷ | XVIII |
| COOCH²⁶SCOR²⁷ | XIX |
| COOCR²⁶COR²⁷ | XX |
| COOCR²⁶OR²⁷ | XXI |
| COOCOOR²⁷ | XXII |
| COOCHR²⁶OCOOR²⁷ | XXIII |
| 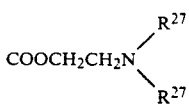 | XXIV |
| COOCHR²⁶OCH₂CH₂OCH₃ | XXV |
| COOCH₂OCO(CH₂)ₜ—CHR²⁸—NH₂ | XXVI |
| 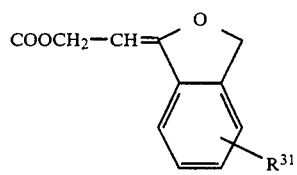 | XXVII |
| 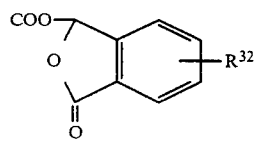 | XXVIII |

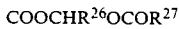
XXIX in which
$R^{26}$ is a hydrogen atom or a 1-6C alkyl radical, $R^{27}$ is a 1-6C alkyl radical, $R^{28}$ is a hydrogen atom, a 1-6C alkyl, 7-11C arylalkyl or a 2-6C alkoxycarbonyl radical, t is 0 or 1, $R^{29}$ is a 1-6C alkyl, 6-10C aryl or 7-11C aralkyl radical, $R^{30}$ is a hydrogen atom or one, two or three substituents selected from halogen atoms and nitro, cyano, 1-6C alkyl, 1-6C alkoxy, 1-6C alkylthio, 1-6C alkanesulphinyl, 1-6C alkanesulphonyl, 2-6C alkoxycarbonyl, 2-6C alkoxythiocarbonyl, 2-6C acylamino, 6-10C aryl, 6-10C aryloxy, 6-10C arylthio 6-10C arenesulphinyl, 7-11C aryloxycarbonyl, 7-11C arylthiocarbonyl, 6-10C arenesulphonyl and 7-11C aryloxythiocarbonyl radicals, $R^{31}$ is a hydrogen atom or one of the values for $R^{29}$ given above and $R^{32}$ is a hydrogen atom or one, two or three substituents selected from halogen atoms and 1-6C alkyl and 1-6C alkoxy radicals, or $R^1$ is a tetrazol-5-yl radical.

Particular values for $R^2$ and $R^3$, which may be the same or different, are hydrogen atoms or methyl, acetyl, hydroxy, methoxy, amino, acetylamino, methylamino, 2-aminoethyl, 2-hydroxyethyl, 2-carboxyethyl, allyl, methoxymethyl, methoxycarbonylmethyl, furylmethyl, phenyl or benzyl radicals, in the latter two of which the phenyl ring is optionally substituted by a fluorine, chlorine or bromine atom or by a methyl, methoxy, nitro, hydroxy, amino, carboxy or methoxycarbonyl radical.

Particular values for $R^4$ and $R^5$, which may be the same or different are fluoromethyl, chloromethyl, bromomethyl, difluoromethyl, trifluoromethyl, azidomethyl, 3-azidopropyl cyanomethyl, 2-cyanoethyl, carboxymethyl, 2-carboxyethyl, methoxycarbonylmethyl, carbamoylmethyl, 2-carbamoylethyl, methylcarbamoylmethyl, dimethylcarbamoylmethyl, 2-amino-2-carboxyethyl, vinyl, allyl, 2-nitrovinyl, 2-phenylvinyl, 1-phenylvinyl, 2-phenylallyl, 3-phenylallyl, 1,2-diphenylvinyl, 2,2-diphenylvinyl, 2,3-diphenylallyl, 3,3-diphenylallyl, 1,2,2-triphenylvinyl, 2,3,3-triphenylallyl, methylthio, 2-aminoethylthio, 2-methylaminoethylthio, 2-dimethylaminoethylthio, 2-aminoethoxy, 2-methylaminoethoxy, 2-dimethylaminoethoxy, phenylthio, phenoxy, benzyl, amino, methylamino, dimethylamino, phenylamino, benzylamino, diphenylamino, formyl; acetyl, benzoyl, methoxycarbonylamino, phenoxycarbonylamino, methoxythiocarbonylamino, phenoxythiocarbonylamino, acetylamino, propionylamino, benzoylamino, 3-methylureido, 3-phenylureido, 3-hydroxyprop-1-enyl, carbamoyl, methylcarbamoyl, dimethylcarbamoyl, 2-dimethylaminoethylcarbamoyl, 3-dimethylaminopropylcarbamoyl, phenylcarbamoyl, thiocarbamoyl, (methyl)thiocarbamoyl, (dimethyl)thiocarbamoyl, (phenyl)thiocarbamoyl, (2-dimethylaminoethyl)thiocarbamoyl, methoxymethyl, 3-methoxypropyl, acetoxymethyl, 3-acetoxypropyl, carbamoyloxymethyl, methylcarbamoyloxymethyl, 3-(methylcarbamoyloxy)propyl, dimethylcarbamoyloxymethyl, (phenyl)(hydroxy)methyl, (phenyl)(amino)methyl, acetylaminomethyl, 2-acetylaminoethyl, 3-acetylaminopropyl, 2-trifluoroacetylaminoethyl, 3-trifluoroacetylaminopropyl, benzoylaminomethyl, ureidomethyl, 3-ureidopropyl, (3-methylureido)methyl, 2-(3-methylureido)ethyl, (3,3-dimethylureido)methyl (3-phenylureido)methyl, guanidinomethyl, formimidoylaminomethyl, methylimidoylaminomethyl, methoxy, formylmethyl, methanesulphonylaminomethyl, 2-(methanesulphonylamino)ethyl, 3-(methanesulphonylamino)propyl or benzenesulphonylaminomethyl radicals or $R^4$ and $R^5$ are ethyl or propyl radicals which are substituted on different carbon atoms by two radicals selected from hydroxy, nitro, amino, methylamino, dimethylamino, phenylamino, benzylamino, (phenyl)(methyl)amino, (benzyl)(methyl)amino, pyrrolidino, piperidino, piperazino, N-methylpiperazino, morpholino, methoxy, methylthio, phenoxy, phenylthio, benzyloxy and benzylthio radicals, or $R^4$ and $R^5$ are ethyl or propyl radicals which are substituted on one carbon atom by a nitro, amino, methylamino, dimethylamino or acetylamino radical and on a different carbon atom by a methyl radical which is itself substituted by two radicals selected from cyano, methoxycarbonyl and acetyl radicals, or $R^4$ and $R^5$ are radicals of the formulae IV, V, VI, VII, VIII, IX or X given above in which Y is an oxygen or sulphur atom or a $CH_2$ radical, m is 1, 2 or 3, q is 0, 1, or 2, n is 0, 1 or 2, p is 1 to 4, $R^{10}$ is a methyl, ethyl, phenyl or benzyl radical, $R^{11}$ is a hydrogen atom or a methyl or phenyl radical, $R^{12}$ is a hydrogen atom or a methyl, phenyl, benzyl or heterocyclyl radical, $R^{13}$ is a hydrogen atom or a methyl or n-propyl radical optionally substituted by a carboxy, methoxycarbonyl, carbamoyl or cyano radical, $R^{14}$ is a heteroacyclyl radical, $R^{15}$ is a hydroxy or amino radical, $R^{16}$ is a pyridyl radical, $R^{17}$, $R^{18}$ and $R^{19}$, which may be the same or different, are hydrogen atoms or methyl or phenyl radicals, and $R^{20}$ and $R^{21}$, which may be the same or different, are cyano, nitro, methoxycarbonyl, phenoxycarbonyl, acetyl or benzoyl radicals, or $R^4$ and $R^5$ are heterocyclic radicals which are linked (to the imidazole ring) by a direct bond or by a methylene or thiomethylene ($SCH_2$) bridge, or $R^4$ and $R^5$ are hydrogen, fluorine, chlorine or bromine atoms or methyl, cyano, hydroxy, carboxy, methoxycarbonyl, aminomethyl, 2-aminoethyl, methylaminomethyl, dimethylaminomethyl, hydroxymethyl or 2-hydroxyethyl radicals or phenyl radicals optionally substituted by 1 or 2 radicals selected from fluorine, chlorine and bromine atoms and nitro, amino, hydroxy carboxy, cyano, methyl and methoxycarbonyl radicals, or $R^4$ and $R^5$ are joined to form, together with the carbon atoms to which they are attached, a mono-, bi- or tricyclic carboxylic ring system which may be non-aromatic, partially aromatic or fully aromatic, the aromatic part of such a ring system being optionally substituted by 1, 2 or 3 substituents selected from fluorine, chlorine and bromine atoms and hydroxy, amino, cyano, carboxy, carbamoyl, nitro, ureido, methyl, methoxy, trifluoromethyl, methylamino, hydroxymethyl, 2-hydroxyethyl, aminomethyl, 2-aminoethyl, acetylamino, azidomethyl, dimethylamino, 2-methylaminoethyl, 2-dimethylaminoethyl, cyanomethyl, carboxymethyl, carbamoylmethyl and ureidomethyl radicals and radicals of the formulae XI, XII, XIII, XIV, XV, and XVI given above in which e is 0 to 6, f is 4 to 8 and $R^{22}$, $R^{23}$, $R^{24}$, and $R^{25}$, which may be the same or different, are hydrogen atoms or methyl radicals;

wherein when $R^4$ or $R^5$ contains a phenyl radical, that phenyl radical may optionally be substituted by 1 or 2 substituents selected from fluorine, chlorine and bromine atoms and nitro, amino, hydroxy, carboxy, cyano, methyl, methoxy, carbonyl, sulpho, methoxy, trifluoromethyl, methylsulphamoyl, dimethylsulphamoyl and dimethylamino radicals, and wherein, when $R^4$ and $R^5$ contains a heterocyclic radical, that radical is a furan, thiophene, pyrrole, oxoazole, thiazole, imidazole, isoxazole, isothiazole, thiadiazole, oxadiazole, triazole, tetrazole, pyridine, pyrimidine, pyrazine, pyridazine or piperazine ring, such ring, were possible, optionally being in the form of the N-oxide, such ring being optionally fused with a benzene ring and such fused benzene ring and/or (where possible) heterocyclic ring being optionally substituted by one or two substituents selected from fluorine, chlorine and bromine atoms and methyl, ethyl, hydroxy, methoxy, phenoxy, mercapto, methylthio, phenylthio, carboxy, methoxycarbonyl, phenoxycarbonyl, carbamoyl, methylcarbamoyl, dimethylcarbamoyl, phenylcarbamoyl, diphenylcarbamoyl, nitro, amino, methylamino, dimethylamino, phenylamino, (phenyl)(methyl)amino, diphenylamino, carboxyamino, (carboxy)(methyl)amino, (carboxy)(phenyl)amino, acetylamino, (acetyl)(methyl)amino, benzoylamino, (benzoyl)(methyl)amino, cyano, phenyl, sulphamoyl, methylsulphamoyl, dimethylsulphamoyl, phenylsulphamoyl, trifluoromethyl, 2,2,2-trifluoroethyl, 2-aminoethyl, 2-methylaminoethyl, 2-dimethylaminoethyl, 2-carboxyethyl, 2-sulphoethyl and oxo radicals.

Particular values for $R^6$, $R^7$, $R^8$, and $R^9$, which may be the same or different, are selected from hydrogen atoms and carboxy, cyano, pyridyl, acetyl, hydroxymethyl, methyl, ethyl, n-propyl, n-hexyl, phenoxymethyl, (in which the phenoxy part is optionally substituted by a diphenylmethyl) and phenyl radicals, the phenyl radicals being optionally substituted by 1, 2 or 3 substituents selected from fluorine, chlorine and bromine atoms and cyano, amino, carboxy, carbamoyl, hydroxy, phenyl, phenoxy, diphenylmethyl, methylamino, acetylamino, methanesulphonylamino, aminomethyl, hydroxymethyl, dimethylamino, methoxycarbonyl, methylcarbamoyl and dimethylcarbamoyl radicals, or $R^7$ and $R^8$, when in the cis relationship, are joined to form, together with the carbon atoms to which they are attached, a 3 to 6 membered carboxylic ring, the ring being optionally substituted by 1 or 2 radicals selected from phenyl and trifluoromethyl radicals and the 4 to 6 membered rings optionally containing a double bond in a position other than at the ring fusion.

The following are eight preferred features of the penicillin derivative of the formula I. When any one of these features is taken, either singly or in combination, with the other general features of the penicillin derivative of the formula I listed above, there are obtained preferred sub-groups of compounds within the above general definition.

1. $R^1$ is a carboxy radical.
2. $R^1$ is a pivaloyloxymethoxycarbonyl radical.
3. $R^2$ is a hydrogen atom.
4. $R^2$ is a methyl radical.
5. X is a nitrogen atom.
6. A< is a radical of the formula III in which $R^6$, $R^7$, $R^8$ and $R^9$ are hydrogen atoms.
7. A< is a radical of the formula II in which $R^4$ and $R^5$ are joined to form an unsubstituted benzene ring.
8. A< is a radical of the formula II in which $R^5$ is a hydrogen atom and $R^4$ is a hydrogen atom or a methyl radical.

Particular compounds of the invention are described in the Examples. The following is a group of preferred compounds:

6-(benzimidazol-2-yl)amino-2,2-dimethylpenam-3-carboxylic acid (Example 2);

2,2-dimethyl-6-(imidazol-2-yl)aminopenam-3-carboxylic acid (Example 4);

2,2-dimethyl-6-(4-methylimidazol-2-yl)aminopenam-3-carboxylic acid (Example 5);

and the pharmaceutically-acceptable acid-addition salts and base-addition salts thereof.

A suitable acid-addition salt of the penicillin derivative of the invention is, for example, a salt formed with hydrochloric, hydrobromic, phosphoric, sulphuric, citric or maleic acid. A suitable base-addition salt of the penicillin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N¹-dibenzylethylenediamine, and other amines which have been used to form salts with penicillins).

The penicillin derivative of the formula I may be manufactured by methods known in themselves for the manufacture of chemically analogous compounds. The following processes, $R^1$, $R^2$, A and X having the meanings stated above, unless indicated otherwise, are therefore provided as further features of the invention.

The process of the invention is characterised by:

(a) for those compounds in which $R^1$ is a carboxy radical or a heterocyclic radical carrying an acidic proton, and there is optionally a carboxy radical in another part of the molecule, deprotection of the corresponding compound which carries a protecting group, or groups, in place of the acidic hydrogen atom, or atoms. When $R^1$ is a carboxy radical useful protecting groups are the trimethylsilyl radical (removed by water), the benzyl and substituted benzyl radicals, for example the p-nitrobenzyl or p-methoxybenzyl radical, (removed by hydrogenolysis) and the 2,2,2-trichloroethyl radical (removed by zinc/acetic acid).

(b) reaction of a compound of the formula XXX:

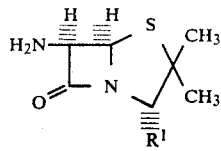

with a compound of the formula XXXI:

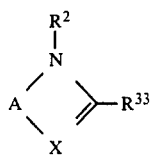

in which $R^{33}$ is a displaceable radical. $R^{33}$ is, for example, a halogen atom, preferably a fluorine or chlorine atom. When $R^2$ is a hydrogen atom, the compound of the formula XXXI may conveniently be prepared in situ by prior reaction of the corresponding N-triphenylmethyl derivative with toluene-p-sulphonic acid. The compound of the formula XXX is then added to the reaction mixture.

(c) for those compounds in which $R^2$ is other than a hydrogen atom and X is a nitrogen atom, reaction of a compound of the formula XXX with a compound of the formula XXXII:

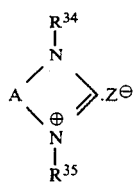

in which $R^{34}$ has the value given above for $R^2$ other than a hydrogen atom, $R^{35}$ is a displaceable radical and $Z^\ominus$ is an anion. $R^{35}$ is, for example, a 1-6C alkoxy or 1-6C alkylthio radical, for example a methoxy or methylthio radical. $Z^\ominus$ is, for example, a halide anion, for example a chloride, bromide or iodide, or a methanesulphonate or toluene-p-sulphonate.

Or (d) for those compounds in which $R^2$ is a hydrogen atom, replacement by hydrogen or the radical $R^{36}$ in a compound of the formula XXXIII:

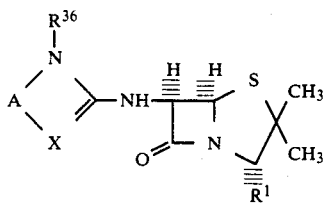

in which $R^{36}$ is a hydroxy, methoxy or methylthio radical. The process may be carried out using titanium trichloride.

When the process of the invention manufactures the compound of the formula I in the form of the free acid or free base, or the zwitterion, and a salt is required, the compound of the formula I in the free acid or zwitterionic form is reacted with a base which affords a pharmaceutically-acceptable cation, or the compound of the formula I in the free base or zwitterionic form is reacted with an acid which affords a pharmaceutically-acceptable anion. When the process of the invention manufactures the compound of the formula I in the form of an acid-addition salt and the zwitterionic form is required, the compound of the formula I in the form of the acid-addition salt is reacted with a low molecular weight epoxide such as epoxypropane.

As noted above the penicillin derivatives of the invention have antibacterial properties, having such effects in vitro against standard laboratory microorganisms, both Gram-negative and Gram-positive, which are used to screen for activity against pathogenic bacteria. The antibacterial spectrum and potency of a particular compound may be determined in a standard test system. The results set out in the following Table are illustrative of the biological activity displayed by the three chemical sub-types (imidazoles, benzimidazoles and 2-imidazolines) contained in this patent application on such an in vitro test system using Jewell and Pearmain agar medium. The antibacterial activity is described in terms of the minimum inhibitory concentration (MIC) determined by agar-dilution technique with an inoculum size of $\sim 10^5$ CFU.

known drugs selected from other clinically useful antibacterial agents (for example other β-lactams or aminoglycosides), inhibitors of β-lactamase (for example clavulanic acid), renal tubular blocking agents (e.g. probenicid) and inhibitors or metabolising enzymes (for example inhibitors or peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the penicillin derivative, or one suitable for oral administration in unit dosage form, for example a tablet or capsule which contains between 100 mg. and 1 g. of the penicillin derivative.

The pharmaceutical composition of the invention will normally be administered to man in order to combat infections caused by bacteria, in the same general manner as that employed for ampicillin, mecillinam, amoxycillin and other known clinically used penicillin derivatives, due allowance being made in terms of dose levels for the potency of the penicillin derivative of the present invention relative to the known clinically used penicillins. Thus each patient will receive a daily intra-

| | | MIC μg/ml. | | |
|---|---|---|---|---|
| Organism | Code No. | $A\diagdown^{R^1}$ H—C(COOH)—H | $A\diagdown^{R^1}$ (benzene)—COOH | $A\diagdown^{R^1}$ $CH_2$—$CH_2$— COOCH$_2$OCOC$_4$H$_9^t$ |
| Strep. pyogenes | A1 | 32 | 8 | 256 |
| Staph. aureus | A6 | 32 | 64 | >256 |
| E. coli | A8 | 0.25 | 128 | 128 |
| Salmonella dublin | A20 | 0.12 | 64 | 32 |
| K. aerogenes | A10 | >256 | >256 | >256 |
| Ent. clocae | A13 | 32 | >256 | >256 |
| Serratia marescens | A16 | 256 | >256 | >256 |
| Proteus mirabilis | A18 | 128 | >256 | 256 |
| Ps. aeruginosa | A21 | >256 | >256 | >256 |

The antibacterial properties of the compounds of the invention may also be demonstrated in conventional mouse protection tests, the compounds being administered subcutaneously. At the minimum effective dose which protected 50% of the mice against bacterial infection, no side effects or overt toxic symptoms attributable to the administered compound were noted.

According to a further feature of the invention there is provided a pharmaceutical composition which comprises a penicillin derivative of the invention in association with a non-toxic pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the penicillin derivative of the formula I the pharmaceutical composition of the invention may also contain, or be co-administered with, one or more venous, subcutaneous or intramuscular dose of 0.5 to 50 g. and preferably 0.5 to to 10 g., of the penicillin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the penicillin derivative, the composition being administered 1 to 4 times per day.

The invention is illustrated, but not limited, by the following Examples. The n.m.r. spectra are quoted in δ relative to the tetramethylsilane (δ=0) as internal standard, (s=singlet, d=doublet, t=triplet, q=quartet, m=multiplet, br=broad). The temperatures are in degrees Centigrade. The following contractions are used:
EtOAc=ethyl acetate
MeOH=methanol
DMF=dimethylformamide
DMSO=dimethylsulphoxide ether = diethyl ether In the Examples the penicillin derivative of the invention is isolated in the form of a salt, either an internal salt (a zwitterion) or a salt with an acid such as HCl or toluene-p-sulphonic acid. The actual salt which is isolated is dependent on a number of factors including the basicity of the product, the reaction, work-up and purification conditions used and the nature of the starting material (salt or free base).

EXAMPLE 1

A mixture of pivaloyloxymethyl 6-amino-2,2-dimethylpenam-3-carboxylate toluene-p-sulphonate (200 mg.) and 2-fluorobenzimidazole (108 mg.) in methylene chloride (2 ml.) was stirred at ambient temperature for 3 hours. The reaction mixture was evaporated to dryness and the residue was triturated with ether and hexane to give pivaloyloxymethyl 6-(benzimidazol-2-yl)amino-2,2-dimethylpenam-3-carboxylate toluene-p-sulphonate (170 mg.) as a solid which had the following n.m.r. spectrum in $d_6$DMSO: 1.14 (s, 9H); 1.43 (s, 3H); 1.60 (s, 3H); 2.24 (s, 3H); 4.55 (s, 1H); 5.5–5.9 (m, 4H); 7.0–7.54 (m, 8H).

EXAMPLE 2

To a solution of anhydrous 6-amino-2,2-dimethylpenam-3-carboxylic acid toluene-p-sulphonate (171 mg.) in dry DMF was added 2-fluorobenzimidazole (150 mg.) in one portion and the mixture stirred at ambient temperature for 1.5 hours. The mixture was evaporated to dryness under reduced pressure at room temperature and the resulting residue, a mobile oil, was triturated with EtOAc (2×10 ml.) and then dry acetonitrile (2 ml.) whereupon the product crystallised. The solid was filtered and washed with acetonitrile and ether to give 6-(benzimidazol-2-yl)amino-2,2-dimethylpenam-3-carboxylic acid toluene-p-sulphonate (185 mg.), m.p. 181°–183°, having the following n.m.r. spectrum in $d_6$DMSO: 1.49 (s, 3H); 1.62 (s, 3H); 2.29 (s, 3H); 4.39 (s, 1H); 5.54 (br, 1H); 5.68 (d, 1H); 7.0–7.56 (m, 8H); 9.93 (br, 1H).

EXAMPLE 3

6-Amino-2,2-dimethylpenam-3-carboxylic acid (324 mg.) was dissolved in phosphate buffer at pH 7 using one equivalent of NaHCO$_3$. To the stirred solution was added 1-methyl-3-methoxybenzimidazolium methanesulphonate and stirring was continued for 6 hours at ambient temperature. The white solid which precipitated was filtered, washed with ice-cold water and dried in vacuo over P$_2$O$_5$ to give 2,2-dimethyl-6-(1-methylbenzimidazol-2-yl)aminopenam-3-carboxylic acid dihydrate (186 mg.) having the following n.m.r in $d_6$DMSO: 1.5 (s, 3H); 1.65 (s, 3H); 3.6 (s, 3H); 4.25 (s, 1H); 5.55 (m, 2H); 6.9–7.4 (m, 4H).

EXAMPLE 4

A solution of p-nitrobenzyl 2,2-dimethyl-6-(imidazol-2-yl)aminopenam-3-carboxylate toluene-p-sulphonate (360 mg.) in a mixture of ethanol (18 ml.) and CH$_2$Cl$_2$ (5 ml.) was hydrogenated at atmospheric pressure for 3 hours in the presence of 10% w/w palladium-on-carbon (180 mg.). The mixture was filtered, the filtrate evaporated and the residual yellow gum triturated with ether to give 2,2-dimethyl-6-(imidazol-2-yl)aminopenam-3-carboxylic acid toluene-p-sulphonate as a yellow solid (258 mg.) having the following n.m.r. in $d_6$DMSO: 1.5 (s, 3H); 1.6 (s, 3H); 2.30 (s, 3H); 4.35 (s, 1H); 5.46 (d, 1H); 5.66 (d, 1H); 6.97 (s, 2H); 7.10 (d, 2H); 7.50 (d, 2H); 8.7–9.0 (br, 1H). By integration the product was 50% pure and contained 2 moles of toluene-p-sulphonic acid per mole of β-lactam.

The p-nitrobenzyl 2,2-dimethyl-6-(imidazol-2-yl)aminopenam-3-carboxylate toluene-p-sulphonate used as starting material may be prepared as follows:

A mixture of p-nitrobenzyl 6-amino-2,2-dimethylpenam-3-carboxylate toluene-p-sulphonate (523 mg.) and 2-fluoroimidazole (100 mg.) in acetonitrile (2 ml.) was stirred at 50° for 3 hours. The resulting solution was evaporated to dryness and the residue obtained was triturated with ether to give p-nitrobenzyl 2,2-dimethyl-6-(imidazol-2-yl)aminopenam-3-carboxylate toluene-p-sulphonate as a 50% pure solid (572 mg.) which was used without further purification.

EXAMPLE 5

A mixture of p-nitrobenzyl 2,2-dimethyl-6-(4-methylimidazol-2-yl)aminopenam-3-carboxylate toluene-p-sulphonate (200 mg.) and 10% w/w palladium-on-carbon in ethanol (12 ml.) and methylene chloride (3 ml.) was shaken under hydrogen at atmospheric pressure for 3.5 hours. The mixture was filtered, the filtrate evaporated to dryness and the residual gum triturated with ether to give 2,2-dimethyl-6-(4-methylimidazol-2-yl)aminopenam-3-carboxylic acid toluene-p-sulphonate as a yellow powder (118 mg.) having the following n.m.r. in $d_6$DMSO+CD$_3$COOD: 1.5 (s, 3H); 1.6 (s, 3H); 2.11 (s, 3H); 2.3 (s, 3H); 4.35 (s, 1H); 5.40 (d, 1H); 5.62 (d, 1H); 6.72 (s, 1H); 7.1 (d, 2H); 7.5 (d, 2H); 8.76 (s, 1H). The sample was approximately 50% pure.

The p-nitrobenzyl 2,2-dimethyl-6-(4-methylimidazol-2-yl)aminopenam-3-carboxylate used as starting material may be prepared by repeating the second part of Example 4 using 2-fluoro-4-methylimidazole in place of 2-fluoroimidazole. The product from this reaction was used without further purification.

EXAMPLE 6

A solution of pivaloyloxymethyl 6-amino-2,2-dimethylpenam-3-carboxylate (250 mg. obtained from the toluene-p-sulphonate salt by washing with aqueous sodium bicarbonate in the presence of methylene chloride) in acetonitrile (6 ml., dried over 4A molecular sieve) was treated under argon with 2-chloro-2-imidazoline hydrochloride (110 mg.) and powdered 4A molecular sieve and the mixture stirred at ambient temperature for 19 hours. The mixture was filtered and the colourless filtrate evaporated to dryness. The residue was purified by low temperature column chromatography on silica gel using MeOH/CH$_2$Cl$_2$ 1:9 v/v as eluant. The appropriate fractions were combined and evaporated and the residue was triturated with anhydrous ether to give pivaloyloxymethyl 2,2-dimethyl-6-(2-imidazolin-2-yl)aminopenam-3-carboxylate HCl as hydroscopic amorphous solid (93 mg.) having the following n.m.r. in D$_2$O: 1.2 (s, 9H); 1.48 (s, 3H); 1.62 (s, 3H); 3.75 (s, 4H); 5.32 (d, 1H); 5.7 (d, 1H); 5.82 (d, 1H); 5.95 (d, 1H).

What we claim is:

1. A penicillin derivative of the formula I:

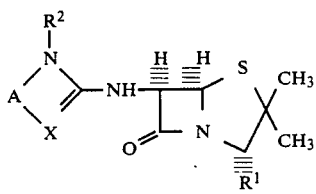

in which $R^1$ is a carboxy radical or a radical of the formula $COOCHR^{26}OCOR^{27}$ wherein $R^{26}$ is hydrogen or 1–6C alkyl, $R^{27}$ is 1–6C alkyl, $R^2$ is hydrogen or methyl; A< is a radical of the formula II or formula III:

   II

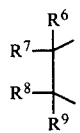   III wherein $R^4$ and $R^5$ are hydrogen or 1–6C alkyl or are joined together to form a benzene ring, $R^6$–$R^9$ are hydrogen, and X is nitrogen, or a pharmaceutically-acceptable acid- or base-addition salt thereof.

2. A penicillin derivative as claimed in claim 1 in which A< is a radical of the formula III in which $R^6$, $R^7$, $R^8$ and $R^9$ are hydrogen or A< is a radical of the formula II in which $R^5$ is hydrogen and $R^4$ is hydrogen or methyl, or $R^4$ and $R^5$ are joined to form an unsubstituted benzene ring.

3. The compounds 6-(benzimidazol-2-yl)amino-2,2-dimethylpenam-3-carboxylic acid, 2,2-dimethyl-6-(imidazol-2-yl)aminopenam-3-carboxylic acid and 2,2-dimethyl-6-(4-methylimidazol-2-yl)aminopenam-3-carboxylic acid, and the pharmaceutically-acceptable acid- and base-addition salts thereof.

4. A pharmaceutical composition which comprises a penicillin derivative as claimed in claim 1 in association with a pharmaceutically-acceptable diluent or carrier.

5. A method of treating a bacterial infection in a warm blooded animal which comprises administering to the animal a therapeutically effective amount of a compound of claim 1.

6. A compound selected from the group consisting of 2,2-dimethyl-6-(imidazol-2-yl)aminopenam-3-carboxylic acid, and the pharmaceutically acceptable acid- and base-addition salts thereof.

* * * * *